United States Patent [19]

Colby

[11] 4,229,594
[45] Oct. 21, 1980

[54] PREPARATION OF META-PHENOXYTOLUENE

[75] Inventor: Thomas H. Colby, Houston, Tex.

[73] Assignee: Shell Oil Company, Houston, Tex.

[21] Appl. No.: 38,601

[22] Filed: May 14, 1979

Related U.S. Application Data

[63] Continuation of Ser. No. 891,951, Mar. 31, 1978, abandoned.

[51] Int. Cl.$^3$ ............................................. C07C 41/01
[52] U.S. Cl. ................................................... 568/635
[58] Field of Search ....................................... 568/635

[56] References Cited

FOREIGN PATENT DOCUMENTS 42-6811 10/1967 Japan .
1415945 12/1975 United Kingdom .

OTHER PUBLICATIONS

Moroz et al., Russian Chemical Reviews, vol. 42 (1974), pp. 679-689.
Mushiaki et al., Chem. Abs., vol. 71 (1969), 12817a.

*Primary Examiner*—Bernard Helfin

[57] ABSTRACT

Meta-phenoxytoluene is prepared by treating particular mixtures of sodium and potassium meta-cresylates with an excess of chlorobenzene, under essentially anhydrous conditions, in the presence of meta-cresol, and cuprous chloride as catalyst, at temperatures within the range of from about 150° C. to about 170° C.

3 Claims, No Drawings

PREPARATION OF META-PHENOXYTOLUENE

This is a continuation of application Ser. No. 891,951, filed Mar. 31, 1978 now abandoned.

BACKGROUND OF THE INVENTION

As is described in U.S. Pat. No. 4,014,940, mixtures of metaphenoxybenzyl bromide and meta-phenoxybenzal bromide are of interest as precursors for the preparation of insecticidal esters of certain cyclopropanecarboxylic acids, and these bromides can be prepared by brominating meta-phenoxytoluene.

It is therefore desirable to have available an efficient process for preparing meta-phenoxytoluene.

DESCRIPTION OF THE INVENTION

It has been found that meta-phenoxytoluene can be prepared in a highly efficient manner by treating mixtures of sodium and potassium meta-cresylates containing at least forty percent potassium cresylate, with at least a ten percent stoichiometric excess of chlorobenzene, under essentially anhydrous conditions, in the presence of at least about 0.5 mole of meta-cresol and from about 0.01 to about 0.05 mole of cuprous chloride, per mole of said mixture of cresylates, at a temperature within the range of from about 150° C. to about 170° C.

This process effects conversion of about 75-85% of the cresylates, with selectivity of 90% or more with regard to both the cresylates and the chlorobenzene, giving yields of meta-phenoxytoluene of the order of about 80-85%.

It has been found that potassium meta-cresylate is suitable in this process, and that sodium meta-cresylate is not, but that mixtures of the two containing at least forty mole percent potassium meta-crysylate are quite suitable. Both the rate of the reaction and the conversion of the cresylates tend to increase with an increase in the proportion of the potassium salt. Accordingly, it is preferred that the mixture contain at least about fifty percent of the potassium salt. Since sodium hydroxide is much less expensive than potassium hydroxide, the equimolar mixture is to be preferred, from the standpoint of economy.

The treatment must be conducted under essentially anhydrous conditions. By this is meant that the amount of moisture in the reaction mixture must not exceed about 2000 parts by weight per million parts by weight of the reaction mixture, and preferably does not exceed about 1500 parts per million on the same basis. Thus, the cresylates, the metal-cresol, the cuprous chloride and the chlorobenzene all must be as free from water as possible, and provision must be made for excluding water from the reaction zone. The presence of water adversely effects the catalyst.

The cresylates are known compounds. If not readily available commercially, they can be prepared by treating meta-cresol with sodium and potassium hydroxides in the appropriate proportions, in the presence of water, and then dehydrating the resulting mixture. For use in the process of this invention, the mixture of cresylates is conveniently prepared by conducting the treatment of meta-cresol with the hydroxides in an excess of the cresol, then dehydrating the mixture by distilling off the water and some of the cresol simultaneously, to leave a solution of the cresylates in the cresol that is suitably free from moisture for use directly in the process of this invention. The amount of cresol used at the outset must of course be sufficient to provide the cresylates, to enable removal of the water, and to supply the amount needed in the treatment of the cresylates with the chlorobenzene.

To attain a practically rapid reaction rate in the treatment of the cresylates with the chlorobenzene, it is necessary that there be present at least about 0.5 mole of meta-cresol per mole of the cresylates, and the reaction rate tends to increase as the amount of cresol present is increased. However, little additional such advantage arises from the use of more than about 0.9 mole of meta-cresol per mole of the cresylates, and this is balanced by the increased inventory of cresol and the need for its storage and handling. In most cases it will be found on balance that the use of from about 0.6 to about 0.8 moles of cresol per mole of cresylates will be preferable.

To attain a practically rapid reaction rate it also is necessary to use at least about 0.01 mole of cuprous chloride, as catalyst, per mole of the cresylates. However, more than about 0.035 mole of cuprous chloride, on the same basis, causes the reaction to proceed so rapidly that it is difficult to control the heat generated by the reaction. It will be found preferable to use from about 0.02 to about 0.03 mole of cuprous chloride per mole of cresylates.

The permitted temperature of the reaction mixture also is fixed by process considerations: at temperatures below about 150° C., the reaction of the cresylates with the chlorobenzene proceeds at an undesirably low rate, while at temperatures above about 170° C., the catalyst tends to decompose too rapidly. Preferably a temperature of about 155°–165° C. is used, with temperatures of about 160° C. being optimum.

It has been found that the catalyst degrades during the treatment of the cresylates with the chlorobenzene, and that the useful life of the catalyst under the conditions specified herein is about four hours, which is the usual time required in the process of the invention for effectively converting the cresylates to meta-phenoxytoluene.

An excess of from about 0.10 to about 0.5 mole of chlorobenzene per mole of cresylates is used. At lower amounts of chlorobenzene, the yield of meta-phenoxytoluene tends to fall, while larger amounts of chlorobenzene result in relatively small increases in the yield, but require the recycling of larger amounts of chlorobenzene. On balance, it appears that use of an excess of from about 0.15 to about 0.4 mole of chlorobenzene per mole of cresylates is to be perferred.

One preferred technique for conducting the treatment of the cresylates with the chlorobenzene is to form the essentially anhydrous solution of the cresylates, as has already been described herein, add essentially anhydrous cuprous chloride, then begin addition of the chlorobenzene, controlling the rate of addition to maintain a reaction mixture temperature of about 160° C., refluxing the chlorobenzene to maintain that level readily. When all of the chlorobenzene has been added, and sufficient has been reacted to reduce the mixture volatility, the pressure in the reaction mixture is reduced to remove heat of reaction and maintain the temperature by boiling the reaction mixture.

The meta-phenoxytoluene can be recovered as follows:

(a) The final reaction mixture is cooled and water is added to dissolve the sodium and potassium chlorides that have been formed; two liquid phases form.

(b) At this point, part of the copper originally charged will have been converted to a red-brown solid. This can be removed by filtering the entire two-phase mixture. However, it has been found that removal of the solid is much facilitated if the mixture (which is basic) is first acidified to a pH of about 2 to 1 with, for example, hydrochloric acid. Also, since the solid is finely divided, use of a filter aid may be found advantageous.

(c) The two liquid phases are separated.

(d) The organic phase is washed with dilute hydrochloric acid.

(e) The aqueous phase is extracted with chlorobenzene.

(f) The extract and washed organic phase are combined and distilled to remove the chlorobenzene.

Conduct of the process of the invention in practicular instances is described in the following examples. In these examples, the reactions described were conducted in a 10-gallon glass-lined autoclave. In each case, an anhydrous solution of equimolar amounts of potassium and sodium m-cresylates in m-cresol was formed by the procedure that has already been described herein, the catalyst was added thereto, the mixture was heated to 160° C., and the chlorobenzene was added thereto in such a manner as to readily permit close control of the reaction mixture temperature at 160° C., also as described hereinbefore. The already described procedure for isolating the product meta-phenoxytoluene was employed. Table I sets out the particulars and the results.

TABLE 1

| Charge to Reactor, moles | Example Number | |
|---|---|---|
| | 1 | 2 |
| meta-cresol | 48.30 | 48.70 |
| potassium meta-cresylate | 30.00 | 30.00 |
| sodium meta-cresylate | 30.00 | 30.00 |
| copper chloride | 1.78 | 1.78 |
| chlorobenzene | 67.70 | 88.10 |
| Yield of meta-phenoxytoluene, mole %, basis cresylates | 82.00 | 86.30 |
| Conversion of cresylates, mole % | 85.7 | — |
| Conversion of chlorobenzene mole %, basis chlorobenzene charged | 74.6 | — |

TABLE 1-continued

Data obtained from these, and other similar experiments, established the metes and bounds of the process of the invention that have already been described herein, with respect to (a) the suitable cresylate mixtures;

(b) the need for meta-cresol in the treatment of the cresylates with chlorobenzene;

(e) the amount of meta-cresol needed;

(f) the amount of chlorobenzene needed;

(g) the need for excluding water;

(h) the amount of catalyst;

(i) the reaction mixture temperatures.

I claim:

1. A process for preparing meta-phenoxytoluene which comprises treating a mixture of sodium and potassium meta-cresylates containing at least fifty mole percent of potassium meta-cresylate, with from 1.1 to about 1.5 moles of chlorobenzene per mole of said cresylates, under essentially anhydrous conditions, in the presence of from about 0.5 to about 0.9 mole of meta-cresol and from about 0.01 to about 0.035 mole of cuprous chloride per mole of said cresylates, at a temperature within the range of from about 150° C. to about 170° C.

2. A process according to claim 1 wherein an equimolar mixture of sodium and potassium meta-cresylates is used, from about 1.15 to about 1.4 mole of chlorobenzene, from about 0.6 to about 0.8 mole of meta-cresol and from about 0.02 to about 0.03 mole of cuprous chloride are used per mole of the cresylates, and the temperature is within the range of from about 155° to about 165° C.

3. A process according to claim 2 wherein the temperature is about 160° C.

* * * * *